United States Patent [19]

Morishita et al.

[11] 3,943,063

[45] Mar. 9, 1976

[54] PREPARATION OF MICROCAPSULES

[75] Inventors: Masataka Morishita; Yoshihito Inaba; Mitsuru Fukushima; Sadami Kobari; Akiho Nagata; Jinnosuke Abe, all of Shizuoka, Japan

[73] Assignee: Toyo Jozo Company, Ltd., Japan

[22] Filed: Jan. 2, 1973

[21] Appl. No.: 320,180

[30] Foreign Application Priority Data
Dec. 30, 1971  Japan................................ 47-2451

[52] U.S. Cl...................... 252/316; 71/64 F; 264/4; 424/32; 424/33; 424/35; 424/94; 426/302; 427/212
[51] Int. Cl.².......................................... B01J 13/02
[58] Field of Search................ 252/316; 117/100 A; 424/33, 35; 264/4; 427/212

[56] References Cited
UNITED STATES PATENTS

| | | | |
|---|---|---|---|
| 3,173,878 | 3/1965 | Reyes.................................. | 252/316 |
| 3,523,907 | 8/1970 | Vrancken et al................... | 252/316 |
| 3,576,760 | 4/1971 | Gould et al........................ | 424/32 X |
| 3,669,899 | 6/1972 | Vassiliades et al................ | 252/316 |
| 3,714,065 | 1/1973 | Kitajima et al.................... | 252/316 |
| 3,737,337 | 6/1973 | Schnoring et al................ | 252/316 X |

*Primary Examiner*—Richard D. Lovering
*Attorney, Agent, or Firm*—Craig & Antonelli

[57] ABSTRACT

Microcapsules are made by (a.) dispersing or dissolving a core substance in a film-forming polymer solution, (b.) emulsifying in fine droplets the resulting dispersion or solution in a vehicle which is poorly miscible with the solvent of the polymer solution and which doesn't dissolve said polymer to prepare an emulsion, and (c.) adding to the emulsion a non-solvent for the polymer wherein the non-solvent is miscible with the solvent, poorly miscible with the vehicle, and does not dissolve the polymer, whereby the solvent is removed by being absorbed by non-solvent emulsion droplets to precipitate the polymer film around the core substance.

18 Claims, No Drawings

PREPARATION OF MICROCAPSULES

This invention relates to an improved method for preparation of microcapsules.

Encapsulation methods, which have hitherto been well known, may be classified into two categories.

One of these is so called evaporating method in liquid vehicle, wherein a core substance is dispersed in a polymer solution and the polymer is precipitated in the solution around cores. Fore example, one method (1) is to emulsify a core in an aqueous solution dissolved in a solvent, which is immiscible with said core substance and has a boiling point below 100°C, disperse the thus prepared emulsion in a medium of a hydrophilic aqueous colloid solution and remove the solvent through evaporation. According to another method (2), an aqueous solution of a water-soluble core substance is emulsified into a polymer solution dissolved in a hydrophobic organic solvent to prepare an emulsion (W/O), which is further dispersed into a medium such as an aqueous solution containing surface active agents, a hydrophilic aqueous colloid solution containing salts or an aqueous hemoglobin solution to prepare an emulsion [(W/O)/W] and finally the organic solvent is evaporated to precipitate the polymer around the aqueous solution. An alternative method (3) is to prepare capsules by dispersing a core of aspirin powders into a polymer solution dissolved in an organic solvent and thereafter disperse the dispersion in state of droplets into a concentrated aqueous solution of a salt. The method (1) involves a drawback that the core substance is limited only to an aqueous solution or suspension. Another drawback of this method is that no microcapsule but those containing liquids can be produced. Further drawback is that no solvent having a boiling point higher than that of water can be used for the polymer since a hydrophilic aqueous colloid solution is used as a medium. The method (2) is also unsuitable for encapsulation of a substance unstable to water, since the core is always treated in state of an aqueous solution similarly as in the method (1). Further drawback of this method is that a substance soluble in the solvent cannot be used as a core. The microcapsules obtained according to the method (3) are in such a state that the core aspirins are combined by the polymer as in concrete, so that the core substance may be exposed on the surface.

The other category of methods of microcapsule preparation makes avail of a phase separation between three elements of a polymer, a solvent and a non-solvent. For example, one encapsulation method (4) is to disperse a core into an acetone solution of a polyvinyl acetate and, while stirring the dispersion, add water(-miscible with acetone but non-solvent for polyvinyl acetate) to the dispersion to effect phase separation. Another method (5) is to disperse a core into a tetrahydrofuran solution of a polyvinyl chloride and then throw the dispersion into water(miscible with tetrahydrofuran but non-solvent for polyvinyl chloride) followed by stirring to control particle sizes of microcapsules. Further method (6) for encapsulation is to prepare a uniform solution by dissolving a core and a polymer in a solvent, throwing this solution into a non-solvent and stir the mixture. Still further method (7) is to prepare in advance a dispersion of a core substance in a medium of a non-solvent separately from a polymer solution and then add the polymer solution to coat the dispersed particles. As the method (4) adds the non-solvent(water) in an amount which is equal to or over that of the solvent(acetone), it has a drawback that a particular device is required for a stirring operation. Another drawback is that the particle sizes of capsules are difficult to be controlled since they are dependent on stirring and the manner of addition of non-solvents. The method (5) involves drawbacks that cores are gone out of the polymer solution during stirring and that uniform particle sizes are difficult to be obtained. The method (6) has a drawback that control of uniform particle sizes of capsules is very difficult. Furthermore, it has also a drawback that since the core substance must be less in solubility in the solvent than the polymer, it is very difficult to select a suitable combination thereof and their amounts. In the method (7), a polymer solution is added in a non-solvent. Accordingly, a polymer is liable to be precipitated, so that selective precipitation only around the cores can hardly be effected. For the purpose of attaining an efficient precipitation, it is required to use a non-solvent in amounts by far larger than the solvent or to use a solvent wich has a low boiling point and high vapor pressure.

It has now been found that microcapsules can be made easily by effecting a phase separation between the three elements of a polymer, a solvent and a non-solvent in the fourth element of a vehicle. That is, microcapsules can be made by dispersing or dissolving a core substance into a polymer dissolved in a solvent, emulsifying this dispersion or solution in fine droplets in a vehicle which is poorly miscible with the solvent and then adding a non-solvent which is miscible with the solvent, poorly miscible with the vehicle and does not dissolve the polymer, to the emulsion system, whereby the solvent is removed by being absorbed by the non-solvent emulsion droplets to precipitate the polymer around the cores. It has further been found, that by a suitable combination of a polymer solvent, a non-solvent and a vehcile, a core substance, whether it may be in state of liquid or solid, may be formed into microcapsules. In addition, it is also found that a polymer, whether it may either be hydrophilic or hydrophobic, may be used as a film forming polymer. Furthermore, this method is found to have such advantages that a solvent may be selected from a wide range of solvents; that a core substance unstable to heat may be formed into microcapsules since there is no need of heating; that a core substance unstable to pH may be formed into microcapsules since there is no change in pH; that the amount of a solvent may be smaller by a suitable selection of a vehicle; that capsule particle sizes may easily be controlled since a vehicle different from a solvent and a non-solvent may be selected; that the amount of a non-solvent may be small since it is added in state of an emulsion.

The present invention is based on a number of discoveries as set forth above, and provides an improved method for preparing microcapsules, which is novel, belongs to no category of the prior art and may be called as solvent removal method in emulsified dispersion. Thus, the improved method for microcapsule preparation according to the present invention comprises dispersing or dissolving a core substance in a film forming polymer solution, emulsifying in fine droplets the thus prepared dispersion or solution in a vehicle which is poorly miscible with the solvent of said polymer solution and then adding to the emulsion a non-solvent which is miscible with the solvent of said polymer solution, poorly miscible with the vehicle and does not dissolve the polymer, whereby the solvent is removed by being absorbed by the non-solvent emulsion droplets to precipitate the polymer film around the cores.

An object of the present invention, therefore, is to provide a method for encapsulating a core substance, whether it may either hydrophilic or hydrophobic, into microcapsules. Another object of the present invention is to provide a method for encapsulating a core substance, whether it may either be a liquid or a solid, into microcapsules. It is also an object of the present invention to provide a method for encapsulating a core substance, which is unstable to heat or pH, into microcapsules. Another object of the present invention is to provide a method for microcapsule preparation wherein a polymer, whether it may be either hydrophilic or hydrophobic, may be used as a film forming polymer. Still another object of the present invention is to provide a method for microcapsule preparation wherein a solvent may be selected from a wide range of solvents, which may either be hydrophilic or hydrophobic. Further object of the present invention is to provide a method for microcapsule preparation, wherein a vehicle, which is the fourth element, may either be hydrophilic or hydrophobic, Further object of the present invention is to provide a method for microcapsule preparation, wherein capsule particle sizes may freely be controlled due to the viscosity of a vehicle which may widely be varied, although the vehicle to be used is restricted by a combination of a solvent and a non-solvent. Further object of the present invention is to provide an efficient and economical method for microcapsule preparation, wherein a solvent and a non-solvent may be used in smaller amounts. Further object of the present invention is to provide a method for microcapsule preparation which may be completed in a short time due to efficient removal of a solvent. Still further object of the present invention is to provide a method for microcapsule preparation, which may be very easy in operation and also very cheap by making avail of water as a non-solvent.

The term "poorly miscible" in the specification and claims means a complete immiscibility or a miscibility not more than 15 V/V %.

CORE SUBSTANCE

As mentioned above, one particular feature of the method according to the present invention resides in its wide scope of core substances to be employed. That is, any substance, liquid or solid, which may either be hydrophilic or hydrophobic, may be available. Furthermore, a substance which is unstable to heat or pH may also be used. It may either be soluble or insoluble in a polymer solvent and may be in any state, including liquids, solutions, pastes, solids, etc. For example, there may be mentioned such substances in various fields as drugs, enzymes, microorganisms, foods, agricultural medicines, fertilizers, perfumes, dyes, adhesives, etc. It is only required, however, that such substances as reactive with a polymer solution or a vehicle to be employed in the present invention should be excluded from the scope of the present invention.

POLYMER

As another aspect of the method according to the present invention, a wide variety of polymers, either natural or synthetic, may be used as film forming polymers for microcapsules. They may include vinyl polymers or copolymers such as polystyrenes, polyacrylonitriles, polyvinyl chlorides, polyvinyl acetates, polyvinyl alcohols, polyvinyl formals, polyvinyl pyrrolidiones, styrene-acrylonitrile copolymers, styrene-acrylic acid copolymers, styrene-maleic acid copolymers, methyl acrylate-methacrylic acid copolymers, vinylidene chloride-vinyl chloride copolymers, vinyl chloride-vinyl acetate copolymers, vinyl chloride-butyl acetate copolymers, etc. They may also include synthetic resins such as ketone resins, epoxy resins, phenol resins, polyesters, polycarbonates, polyurethanes, polyolefins, etc. They may further include cellulose derivatives such as cellulose acetate, hydroxy propyl cellulose, cellulose acetate phthalate, hydroxy propyl methyl cellulose trimeritate, hydroxy propyl methyl cellulose phthalate, cellulose acetate dibutylaminohydroxy ether, etc. Natural polymers such as gelatin, gum arabic, shellac, etc. may also be used. It is desirable to choose a polymer from a wide range of polymers as mentioned above, which is most fitted for the use of microcapsules.

SOLVENT

Any hydrophilic or hydrophobic solvent may be used as a solvent in the present invention, so long as it can dissolve a polymer and is poorly miscible with a vehicle to be employed. Solvents to be used in the present invention are not restricted to those having low boiling points and high vapor pressures. For example, there may be used hydrocarbons such as benzene, toluene, xylene, etc., alcohols such as methanol, ethanol, isopropanol, etc., ketones such as acetone, methyl ethyl ketone, etc. acids such as formic acid, acetic acid, etc., esters such as methyl acetate and ethyl acetate, organic halides such as ethylene chloride, chloroform, carbon tetrachloride, etc., dimethylformamide, dimethylsulfoxide, and the like. These solvents may be used alone or in mixtures. Water also may be used as a solvent. In case a core substance is encapsulated in state of a liquid or a solution, there should be employed a solvent which is not miscible with such a liquid or a solution and does not dissolve solutes contained therein.

VEHICLE

As a vehicle, there may be used any liquid, either hydrophilic or hydrophobic, which does not dissolve a core substance and a polymer to be employed, is poorly miscible with a solvent to be employed and is capable of emulsifying a polymer solution containing cores in fine droplets. For example, liquid paraffins, silicone oils, ethylene glycol, propylene glycol, polyethylene glycols, formamide, aqueous gelatin solutions, etc. may be used. Since the viscosity of these vehicles may vary depending on the molecular weight, concentration, etc. thereof, it is desirable to choose a vehicle having a viscosity which is suitable for emulsifying a polymer solution to be employed.

NON-SOLVENT

Non-solvents are used in the present invention for the purpose of precipitating polymers from emulsified droplets of a polymer solution suspended in a vehicle by absorbing a polymer solvent. For effective precipitation, therefore, it is only required that a non-solvent should be miscible with a solvent employed and poorly miscible with a vehicle employed, whether it may either be hydrophilic or hydrophobic.

As described above, the present invention allows uses of a considerably wide range of core substances, polymers, solvents, vehicles and non-solvents. However, as already stated above, it is critical that a combination of the four elements, i.e. polymer, solvent, vehicle and non-solvent, should be restricted by the following requirements:

a. Polymer solvents should be poorly miscible with vehicles,
b. Non-solvents should not dissolve polymers,
c. Polymer solvents should be miscible with non-solvents,
d. Non-solvents should be poorly miscible with vehicles, and
e. Vehicles should not dissolve polymers.

For example, when a solvent and a non-solvent are hydrophilic and a vehicle is lipophilic, a solvent is a preferably selected from water, acidic water, alkaline water, acetone, methanol, ethanol, isopropanol, dimethylformamide, formic acid, acetic acid and dimethylsulfoxide, while the non-solvent is preferably selected from water, acidic water, alkaline water, acetone, methanol, ethanol, isopropanol, n-butanol, ethylene glycol, dimethylformamide, tetrahydrofuran and aqueous formalin solution. In this case, a vehicle is preferably a liquid paraffin or a silicone oil. The most preferable result is obtained when water or an aqueous solution is used as a non-solvent. On the other hand, when a solvent and a non-solvent are lipophilic and a vehicle is hydrophilic, a solvent is preferably selected from ethylene chloride, chloroform, methyl acetate, ethyl acetate, benzene, toluene, xylene and carbon tetrachloride, while the non-solvent is preferably selected from hexane, petroleum ether and toluene. In this case, a vehicle is preferably ethylene glycol, propylene glycol, formamide or an aqueous gelatin solution.

Examples of preferable combinations are set forth in Table 1.

Table 1

| Polymer | Solvent | Vehicle | Non-solvent |
|---|---|---|---|
| Hydroxypropyl methyl cellulose phthalate | Acetone-Methanol(5:1) | Liquid paraffin or silicone oil | Water or acidic water |
| Hydroxypropyl methyl cellulose trimeritate | '' | '' | '' |
| Cellulose acetate phthalate | Acetone | '' | '' |
| Methyl acrylate-methacrylic acid copolymer | '' | '' | '' |
| Styrene-acrylic acid copolymer | '' | '' | '' |
| Polyvinylacetal diethylamino acetate | '' | '' | Water or alkaline water |
| Cellulose acetate dibutylaminohydroxypropyl ether | '' | '' | '' |
| Vinylidene chloride-vinyl chloride copolymer | '' | '' | Water |
| Polyvinyl acetate | Acetone or methanol | '' | '' |
| Polyvinyl alcohol | Water | '' | Acetone |
| Ketone resin | Ethanol | '' | Water |
| Epoxy resin | Acetone | '' | '' |
| Phenol resin | Methanol or ethanol | '' | '' |
| Polyvinyl acetate | Methanol | '' | n-butanol |
| Cellulose acetate | Dimethylformamide | '' | Isopropanol |
| Cellulose acetate | '' | '' | n-butanol |
| Styrene-maleic acid copolymer | Ethanol | '' | Acidic water |
| Hydroxypropyl cellulose | Isopropanol | '' | Acetone |
| Cellulose acetate dibutylaminohydroxy propylether | '' | '' | Water or alkaline water |
| Polyvinyl formal | Formic acid or acetic acid | '' | Alkaline water |
| Vinyl chloride-vinyl acetate copolymer | Dimethylformamide | '' | Isopropanol |
| Polyurethane | '' | '' | Water |
| Polyvinyl chloride | '' | '' | Water, methanol, ethanol or isopropanol |
| Polyacrylonitrile | Dimethylformamide or dimethylsulfoxide | '' | Water |
| Shellac | Ethanol | '' | Ethylene glycol |
| Gelatin | Water | '' | Acetone, methanol, ethanol, or isopropanol |
| '' | '' | '' | Aqueous formalin solution |
| '' | '' | '' | Dimethylformamide |
| Gum arabic | '' | '' | Tetrahydrofuran |
| Hydroxypropyl methyl cellulose phthalate | Dimethylformamide | '' | Water or acidic water |
| Cellulose acetate dibutylamino hydroxypropyl ether | '' | '' | Water or alkaline water |
| Cellulose acetate phthalate | '' | '' | Water or acidic water |
| Polyvinylacetal diethylamino acetate | '' | '' | Water or alkaline water |
| Vinyl chloride-vinyl acetate copolymer | Ethylene chloride | Ethylene glycol | n-hexane or petroleum ether |
| Polystyrene | Ethylene chloride or chloroform | '' | '' |
| '' | Methyl acetate or ethyl acetate | '' | '' |
| '' | Benzene | '' | '' |
| Polyester | Ethylene chloride | '' | '' |
| Vinyl chloride-vinyl acetate copolymer | Benzene | Propylene glycol | '' |
| Polyethylene | '' | '' | '' |
| Polycarbonate | Ethylene chloride | Formamide | n-hexane or n-heptane |
| Polyester | Benzene | Ethylene glycol or Propylene glycol | n-hexane or petroleum ether |
| Polyacrylic acid ester | Ethylene chloride or chloroform | '' | Petroleum ether |
| '' | Ethyl acetate | '' | '' |
| Polyvinyl formal | Ethylene chloride or chloroform | '' | Toluene or petroleum ether |
| Cellulose acetate propionate | '' | '' | '' |

Table 1-continued

| Polymer | Solvent | Vehicle | Non-solvent |
| --- | --- | --- | --- |
| " | Ethyl acetate | " | " |
| Cellulose acetate butylate | Ethylene chloride or chloroform | " | " |
| " | Ethyl acetate | " | " |
| Polyvinyl pyrrolidone | Chloroform | " | n-hexane |
| Polyester | Ethylene chloride | Formamide | n-hexane or n-heptane |
| Polyvinyl acetate | Ethylene chloride or chloroform | " | " |
| Vinyl chloride-butyl acetate copolymer | " | " | " |
| Hydroxypropyl methyl cellulose phthalate | Ethylene chloride | " | " |
| Polystyrene | Benzene | " | n-hexane or petroleum ether |
| Vinyl chloride-vinyl acetate copolymer | Ethylene chloride | Aqueous gelatin solution | Petroleum ether |
| Phenyl siloxane ladder polymer | Ethylene chloride or benzene | " | n-hexane or petroleum ether |
| Ethyl cellulose | Xylene | " | Petroleum ether or cyclohexane |
| Polyester | Ethylene chloride | " | n-hexane or petroleum ether |

PROCESS FOR PREPARATION OF MICROCAPSULES

In the present invention, a polymer suitable as a film forming polymer for a core substance is first dissolved in a solvent. If a solvent is used in an amount too much for a polymer, viscosity of emulsified droplets of a polymer solution becomes so low that emulsified droplets may be deformed at the time of addition of a non-solvent to effect leaking of cores therefrom. On the contrary, if the amount of a solvent is too little, viscosity of emulsified droplets becomes too high to be emulsified sufficiently in a vehicle. Thus, viscosity of emulsified droplets or concentration of a polymer may vary depending on a solvent, and a vehicle employed and also on the relative amounts thereof. Accordingly, viscosity of emulsified droplets or concentration of a polymer is determined suitably according to a combination of these elements employed. Although concentration of a polymer may optionally be determined so that viscosity of emulsified droplets may be in the range to permit a sufficient emulsifying dispersion thereof in a vehicle, it is generally in the range from about 0.5 to 20 W/V %. If the concentration is too high, hard microcapsules with thick walls are to be obtained. Thickness of walls is decreased as the concentration becomes lower.

Then a core substance is dispersed or dissolved in the polymer solution as described above to obtain a dispersion or a solution. In order to conduct encapsulation operation easily and also to obtain microcapsules with tough films, it is desirable to use a core substance in an amount from 0.2 to 20 times the amount of a film forming polymer. The dispersion or solution thus prepared is emulsified in fine droplets in a vehicle. The relative amount of the dispersion or solution to the vehicle, which may vary depending on the concentration of a polymer, is generally about from 1:5 to 1:30 V/V.

If surface active agents are in advance to a vehicle before the emulsifying dispersion as mentioned above, emulsifying of a polymer solution is very easy and the state of emulsion is stable to produce favorable results. Alternatively, minute suspension powders may be dispersed in a vehicle. In this case, suspension powders are absorbed by emulsified droplets of microcapsules at the surface thereof to form a part of wall films of microcapsules, whereby adhesion or cohesion between microcapsules may be prevented and the amount of the vehicle may be small to effect an efficient encapsulation. These suspension powders may include those which are referred to as additives, auxiliary agents, fillers, disintegrates, supporting bases, absorbents, binders, moisture proof agents, polishing agents, lubricants, emulsion stabilizing agents, stabilizers, etc. in other fields such as medicaments, agricultural medicines, foods, and the like. Any one of them may be used, so long as it is not soluble in the polymer solvent and does not affect detrimental effect on the core substance (physical property, affinity, etc.). For example, powders of substances such as magnesium stearate, aluminum stearate, aluminum silicate, talc, titanium dioxide and starch may be mentioned. Since dispersing efficiency is variable depending on the particle size, etc. of a suspension powder, it is desirable to select a suspension powder which is most suitable for a combination of a core substance, a polymer, a solvent, a vehicle and a non-solvent as well as the use of microcapusules.

At the beginning, when a polymer solution containing a core substance is added to a vehicle, it is dispersed in extremely fine droplets. The droplets grow bigger by conglomeration as the addition is continued until they become uniform in size. In the step of emulsifying dispersion as mentioned above, fine droplets with various sizes may be obtained depending upon the amount of a solvent, the speed of stirring, the viscosity of a polymer, the viscosity of a vehicle and surface active agents used. Generally, as the stirring speed is more rapid or the viscosity of a polymer solution or a vehicle is lower, emulsified droplets of microcapsules obtained become smaller in size. Particularly, if a core substance is insoluble in a solvent (in case a core substance is dispersed in a polymer solution), the size of a core substance is dependent somewhat on the size of a core substance. On the other hand, when surface active agents are used, the more their amounts are, the smaller are in size the emulsified droplets of microcapsules obtained. Furthermore, when suspension powders are used, the size of emulsified droplets of microcapsules is dependent on the species, particle size or amounts thereof. In this case, minute suspension powders prevent emulsified droplets from adhesion or cohesion with each other, whereby uniformity and stability of the emulsified state is maintained so well as to form emulsified droplets of microcapsules of sizes which are uniform and may freely be controlled.

Finally, a non-solvent is added to the emulsion of a polymer as described above to precipitate the polymer. As a non-solvent is added to the emulsion of a polymer, the solvent is transferred to emulsified droplets of a non-solvent dispersed throughout the vehicle, whereby at the same time precipitation of the polymer occurs to make up microcapsules. A non-solvent may directly and slowly be admixed with the emulsified dispersion of a polymer. Alternatively, a non-solvent dispersed in advance in a vehicle may be added to the dispersion of a polymer. A non-solvent may be used in an amount sufficient to remove the solvents, i.e. an amount which is equal to that of the solvent or more.

The microcapsules precipitated are subsequently collected by separating microcapsules by means of filtration or centrifuge, admixing them well with a vehicle and washing them with a solvent which does not dissolve nor disintegrate microcapsules.

The microcapsules thus obtained are shaped in globular or approximately globular forms and their structures may vary with the state of cores contained therein. If the cores are solids soluble in the solvent employed, the polymer and the cores form a matrix amalgamated in solid state, whereby microcapsules formed show a peculiar distribution of the polymer and the cores with a specific concentration gradient due to the difference between the solubilities thereof in the solvent and the non-solvent employed. For example, if the polymer is higher in solubility than the core substance, the core substance becomes more concentrated at a portion nearer to the center of microcapsules. This phenomenon may be ascribed to the transport of the polymer together with the solvent to the outer, which will presumably occur, at the time when the solvent is transferred into the non-solvent. Although the cross section of the microcapsules having such a structure does not show distinctly border lines between the layers of the polymer and the core substance, such microcapsules can be disintegrated under certain conditions. Thus, microcapsules having such a structure exhibit sufficiently functions as microcapsules for protection of core substances. If suspension powders are used in forming the microcapsules as mentioned above, microcapsules obtained show a structure wherein the suspension powders are attached to near surfaces of the microcapsules, and the layers of the core substance, the polymer and the suspension powders cannot be distinctly discriminated from each other at their cross sections. These microcapsules, however, also exhibit sufficient functions as microcapsules. For example, microcapsules are easily disintegrated in water if suspension powders are strong in wetness or affinity with water, while disintegration thereof is retarded, if reverse are the physical properties of the suspension powders.

On the other hand, if the core substance employed is a solid insoluble in a solvent, a wall film appears to be formed on the surface of microcapsules obtained therefrom, but their cross sections exhibit a state wherein core substances are scattered throughout the matrix of the polymer.

Furthermore, if the core substance employed is a liquid or a solution immiscible with the solvent used and the solutes contained in the solvent are insoluble in the solvent, polymers are precipitated to form film around the cores which remain in their original state and their cross sections exhibit clearly the border lines between the layers of the core substance and the polymer. These microcapsules are excellent in enclosing quality of core substances, and they will not be leaked out of capsules until they are disintegrated under certain conditions.

When water is used as a non-solvent in the process according to the present invention, the polymer films of the microcapsules obtained may be swelled in state of gels to give products which are excellent particularly in semipermeability and may find wide applications.

The present invention will further be explained by referring to the following Examples, in which the core substances, the polymers, the vehicles and the non-solvents are set forth merely for illustrative purposes and not to limit the scope of the present invention.

EXAMPLE 1

Five grams of a cellulose acetate phthalate (product of Wako Junyaku Co.) are dissolved in 60 ml of dimethylsulfoxide to prepare a solution. Into this solution are dispersed 10 g of pancreatin powders of the Japanese Pharmacopeia (product of Iwashiro Seiyaku Co.). This dispersion is emulsified under stirring with a propeller in 300 ml of the liquid paraffin of the Japanese Pharmacopeia(19 cps, 25°C) in fine droplets(200 to 500 $\mu$). Stirring is continued for several minutes until the state of emulsion is stabilized. Then, 100 ml of a mixed solvent of water-acetone(4:1) is added as a non-solvent to the emulsion, whereby microcapsules are formed. The microcapsules are collected by filtration by using a filter cloth, washed thoroughly with n-hexane and dried.

The product obtained is an intestine soluble microcapsule, which on administration is disintegrated not in stomach, but in intestine. Hence, this method is suitable for encapsulation of core substances which are unstable in gastric juice.

EXAMPLE 2

Example 1 is repeated, but the liquid paraffin containing 1.5 g of magnesium stearate dispersed therein is used. The microcapsules obtained are excellent in disintegration quality in living bodies.

EXAMPLE 3

Two grams of a vinyl chloride-vinyl acetate copolymer(product of Denki Kagaku Kogyo K.K.) are dissolved in 20 ml of ethylene chloride to prepare a solution. Into this solution are dispersed uniformly 4 g of alkali phosphatase powders(1 to 5 $\mu$, product of Seikagaku Kogyo Co.). This dispersion is added dropwise into 200 ml of ethylene glycol containing 0.5 % of a surface active agent Lanex(product of Croda Nippon Co.), to prepare an emulsion containing 100 to 150 $\mu$ of emulsified droplets. Then, 100 ml of n-hexane are added slowly to the emulsion, whereby polymer films are precipitated around the cores to give microcapsules containing alkali phosphatase. After filtration, the microcapsules are washed with n-hexane and dried.

The films of the microcapsules obtained are semipermeable membranes, which hydrolyze p-nitro phenylphosphate in an aqueous p-nitro phenylphosphate solution of pH 9.0. This method of microcapsule preparation may therefore be utilized for production of insolubilized enzymes.

EXAMPLE 4

Two grams of an ethyl cellulose(product of Tokyo Kasei Co.) are dissolved in 20 ml of ethylene chloride to prepare a solution. This solution and an aqueous solution, wherein 2 g of an enzyme lipase (product of Meito Sangyo Co.) are dissolved in 4 ml of 0.05 M buffer solution of phosphoric acid (pH 7.0), are emulsified by means of a homogenizer to prepare [W/O] type emulsion. This emulsion is further emulsified in 150 ml of ethylene glycol to prepare a [(W/O)/O] type emulsion. To this emulsion are slowly added under stirring 100 ml of n-hexane to produce microcapsules(100 to 150 $\mu$) wherein the aqueous lipase solution is enclosed by a polymer film. The films of the microcapsules obtained are semipermeable membranes, and the lipase contained therein hydrolyzes p-nitro phenylacetate at high efficiency in the state as enclosed in the capsules.

EXAMPLE 5

Two grams of a polycarbonate resin(product of Teijin Kasei Co.) are dissolved in 20 ml of ethylene chloride to prepare a solution. This solution and 4 ml of an aqueous solution of a group of glycolysis enzymes extracted from muscles of a rabbit are emulsified by means of a homogenizer to prepare a [W/O] type emulsion. This emulsion is further emulsified in 200 ml of formamide. Then 70 ml of n-hexane is gradually added to the emulsion to obtain microcapsules wherein enzyme solutions are enclosed with polymer films. When these microcapsules are dispersed in a phosphoric acid buffer solution containing D-glucose, ATP and NAD(0.05 M, pH 7.0) to carry out a reaction at 37°C for two hours. The substrate glucose incorporated into microcapsules are converted into lactic acid by action of the group of glycolysis enzymes and released out of the capsules.

This method is advantageous in insolubilizing a complex system of enzymes by encapsulation.

EXAMPLE 6

One gram of vinyl chloride-vinylacetate is dissolved in 20 ml of ethylene chloride to prepare a solution. This polymer solution and 3 ml of an aqueous solution containing 100 mg of an enzyme urease (product of Sigma Co.) are emulsified by means of a homogenizer to prepare a [W/O] type emulsion. This emulsion is further emulsified under stirring into 150 ml of 2% aqueous gelatin solution to prepare a [(W/O)/O] type emulsion. To this emulsion is added an emulsion, which is separately prepared by emulsifying 50 ml of n-hexane in 50 ml of 2% aqueous gelatin solution, to obtain microcapsules(50 to 100 $\mu$) wherein aqueous urease solutions are enclosed with in polymeric walls.

It is considered that these microcapsules may be applicable for artifical kidneys.

EXAMPLE 7

Four grams of polyacrylonitrile(product of Asahi Kasei Kogyo K.K.) are dissolved in 20 ml of dimethylsulfoxide to prepare a solution, into which 1 g of urease powders is dispersed. This dispersion is emulsified under stirring in 200 ml of a liquid paraffin of the Japanese Pharmacopeia containing a surface active agent, 0.25% of Span 85 (product of Atlas Co.), to form emulsified droplets with sizes of 150 to 200 $\mu$. Then, 50 ml of water is added to the emulsion as a non-solvent drop by drop in 30 minutes to obtain microcapsules containing urease.

The polymer films of the microcapsules obtained are excellent semipermeable membranes, which hydrolyze urea at high efficiency to release $NH_3$ and $CO_2$.

EXAMPLE 8

Four grams of cellulose acetate are dissolved in 40 ml of dimethylsulfoxide to prepare a solution. Into this solution are uniformly dispersed 4 g of activated carbon (trade name: Shirosagi, product of Nichiyaku Kogyo Co.). The dispersion prepared is then added under stirring to 200 ml of liquid paraffin of the Japanese Pharmacopeia containing 2 ml of Span 85(product of Atlas Co.) to be emulsified in fine droplets. Separately, 100 ml of water is emulsified under stirring into 200 ml of the same liquid paraffin as mentioned above to form a [W/O] type emulsion. This emulsion is added slowly into the emulsion containing activated carbon as prepared above to form microcapsules. These microcapsules are filtered with a filter cloth, washed with n-hexane and further rinsed with acetone containing 50% of water. Thus, 38 g of microcapsules of activated carbon swelled with water are obtained, which are excellent in semipermeability without deteriorating absorption capacity of activated carbon, and also possess selective absorption capacity.

EXAMPLE 9

Two grams of polyacrylonitrile(product of Asahi Kasei Kogyo K.K.) are dissolved in 30 ml of dimethylsulfoxide to prepare a solution. Into this solution are uniformly dispersed dry microorganisms, *Fusarium solani*(FERM-P No. 217, deposited at Fermentation Research Institute, Agency of Industrial Science and Technology, Japan). This dispersion is emulsified in fine droplets in 150 ml of a silicone oil(15 cps, 25°C). To this emulsion are added 80 ml of a mixed solvent of water-acetone(70:30) as a non-solvent in 20 minutes to obtain 24 g of microcapsules. This product is a microcapsule swelled with water containing *Fusarium solani*, a cyan-assimilating fungi, and excellent in water permeability, which may be used for treating drainage containing cyanic compounds.

What we claim is:

1. A process for preparing microcapsules comprising:
dispersing or dissolving a core substance in a film forming polymer solution to prepare a dispersion or a solution thereof,
emulsifying in fine droplets said dispersion or solution in a vehicle which is poorly miscible with the solvent of said polymer solution and which does not dissolve the polymer to prepare an emulsion, and adding to the emulsion a non-solvent for the polymer, wherein the non-solvent is miscible with the solvent, poorly miscible with the vehicle, and does not dissolve the polymer, whereby the solvent is removed by being absorbed by non-solvent emulsion droplets to precipitate the polymer film around the core substance.

2. A process according to claim 1, wherein the solvent and the non-solvent are hydrophilic and the vehicle is lipophilic.

3. A process according to claim 2, wherein the vehicle is selected from the group consisting of liquid paraffins and silicone oils.

4. A process according to claim 2, wherein the solvent is selected from the group consisting of water, acidic water, alkaline water, acetone, methanol, ethanol, isopropanol, dimethylformamide, formic acid, acetic acid, and dimethylsulfoxide and the non-solvent is selected from the group consisting of acetone, methanol, ethanol, isopropanol, n-butanol, ethylene glycol, dimethylformamide, tetrahydrofuran and aqueous formalin solution.

5. A process according to claim 2, wherein the solvent is selected from the group consisting of acetone, methanol, ethanol, isopropanol, dimethylformamide, formic acid, acetic acid, and dimethylsulfoxide and the non-solvent is water or an aqueous solution.

6. A process according to claim 1, wherein the solvent and the non-solvent are lipophilic and the vehicle is hydrophilic.

7. A process according to claim 6 wherein the vehicle is ethylene glycol, propylene glycol, formamide or an aqueous gelatin solution.

8. A process according to claim 6, wherein the solvent is selected from the group consisting of ethylene chloride, chloroform, methyl acetate, ethyl acetate, benzene, toluene, xylene and carbon tetrachloride, and the non-solvent is selected from the group consisting of hexane, petroleum ether and toluene.

9. A process according to claim 1, wherein the film forming polymer is dissolved in a solvent at a concentration of 0.5 to 20 W/V %.

10. A process according to claim 9, wherein the amount of a core substance is 0.2 to 20 times the amount of the film forming polymer.

11. A process according to claim 10, wherein the amount of the vehicle is 5 to 30 times the amount of the film forming polymer solution.

12. A process according to claim 11, wherein the amount of the non-solvent is at least the amount of the solvent.

13. A process according to claim 1, wherein the vehicle contains suspension powders dispersed therein.

14. A process according to claim 1, wherein the solvent is dimethylsulfoxide, the vehicle is liquid paraffin and the non-solvent is water.

15. A process according to claim 14, wherein the polymer is cellulose acetate, ethylcellulose, cellulose acetate phthalate, hydroxypropylmethyl cellulose phthalate, cellulose acetate propionate, cellulose acetate butyrate, cellulose acetate dibutylamino hydroxypropyl ether, polyvinyl chloride, polyvinyl formal, polystyrene, polyacrylonitrile, polyester, polyurethane or vinyl chloridevinyl acetate copolymer.

16. A process for preparing microcapsules consisting of:

dispersing or dissolving a core substance in a film-forming polymer solution to prepare the dispersion or solution thereof;

emulsifying in fine droplets said dispersion or solution in a vehicle which is poorly miscible with the solvent of said polymer solution and which does not dissolve the polymer to prepare an emulsion; and adding to the emulsion a non-solvent for the polymer, wherein the non-solvent is miscible with the solvent, poorly miscible with the vehicle, and does not dissolve the polymer, whereby the solvent is removed by being absorbed by non-solvent emulsion droplets to precipitate the polymer film around the core substance.

17. A process according to claim 16, wherein a core substance is dissolved in a film-forming polymer solution to prepare a solution thereof and said solution is emulsified in fine droplets in said vehicle.

18. A process according to claim 16, wherein the core substance is dispersed in a film-forming polymer solution to prepare a dispersion thereof and the dispersion is emulsified in fine droplets in said vehicle to prepare an emulsion.

* * * * *